US006429935B1

(12) United States Patent
Duan (10) Patent No.: US 6,429,935 B1
(45) Date of Patent: Aug. 6, 2002

(54) MICROWAVE PLASMA MONITORING SYSTEM FOR REAL-TIME ELEMENTAL ANALYSIS

(75) Inventor: Yixiang Duan, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/580,100

(22) Filed: May 26, 2000

Related U.S. Application Data (60) Provisional application No. 60/186,428, filed on Mar. 2, 2000, and provisional application No. 60/186,458, filed on Mar. 2, 2000.

(51) Int. Cl.$^7$ ............................................... G01N 21/73
(52) U.S. Cl. ....................................................... 356/316
(58) Field of Search .......................................... 356/316

(56) References Cited

U.S. PATENT DOCUMENTS

| | | |
|---|---|---|
| 4,844,612 A | 7/1989 | Durr et al. |
| 5,479,254 A | 12/1995 | Woskov et al. |
| 5,671,045 A | 9/1997 | Woskov et al. |

FOREIGN PATENT DOCUMENTS

DE          4004560 A1    8/1990

OTHER PUBLICATIONS

Duan et al, A Field–Portable Plasma Source Monitor for Real–Time Air Particulate Monitoring, Analytical Chemistry, vol. 72, No. 7, Apr. 1, 2000, pp. 1672–1679, Published on the Web Mar. 1, 2000.*

Yixiang Duan et al., "A Field–Portable Plasma Source Monitor for Real–Time Air Particulate Monitoring", Analytical Chemistry, vol. 72, No. 7, 1672 (Apr. 1, 2000).

Duan, Yixiang, Min Yu, Qinhan Jin and Gary M. Hieftje, "Vapor Generation of Nonmetals Coupled to Microwave Plasma–torch Mass Spectrometry," *Spectrochimica Acta Part B*, vol. 50, pp. 1905–1108, 1995.

Duan, Yixiang, Yimu Li, Zhauohui Du, Qinhan Jin and Jose A. Olivares, "Instrumentation and Fundamental Studies on Glow Discharge–Microwave–Induced Plasma (GD–MIP) Tandem Source for Optical Emission Spectrometry," *Applied Spectroscopy*, vol. 50, No. 8, 1996.

(List continued on next page.)

*Primary Examiner*—F. L. Evans
(74) *Attorney, Agent, or Firm*—Gemma Morrison Bennett (57) ABSTRACT

There has been invented a process for analyzing ambient air in a microwave induced plasma without use of an additional carrier gas. There has also been invented an apparatus for analyzing ambient air, other sample gas, or nebulized and desolvated liquids wherein a novel arrangement of plasma gas and sample gas conduits is used to enhance dependability of the plasma. This apparatus embodiment of the invention has a concentric arrangement of plasma gas and sample gas conduits so as to provide a sheath of plasma gas both within and surrounding the flow of analyte into the plasma region. The microwave plasma torch can either be contained within a sealed housing or can be operated in ambient air at ambient pressures. The microwave plasma torch of this invention is portable and can be operated continuously for real-time analysis of air. The apparatuses and methods of the present invention can be used wherever there is a need for monitoring air for the presence of minor amounts of elements, particularly transition metals, rare earth elements, actinides, and alkali and alkaline earth elements. The invention apparatus can also be used to monitor for the presence of halogens, sulfur and silicon. The invention apparatuses and methods are more particularly useful for monitoring air for the presence of beryllium.

10 Claims, 3 Drawing Sheets

OTHER PUBLICATIONS

Woskov, P. P., D. Y. Rhee, P. Thomas D. R. Cohn, J. E. Surma and C. H. Titus, "Microwave Plasma Continuous Emissions Monitor for Trace–Metals in Furnace Exhaust," *Rev. Sci. Instrum.*, 67 (10), Oct. 1996, American Institute of Physics.

Jin, Qinhan, Yixiang Duan and Jose A. Olivares, "Development and Investigation of Microwave Plasma Techniques in Analytical Atomic Spectrometry," *Spectrochimica Acta, Part B*, vol. 52, pp. 131–161, 1997.

Duan, Yixiang, Xiaoguang Du, Yimu Li and Qinhan Jin, "Characterization of a Modified, Low–Power Argon Microwave Plasma Torch (MPT) as an Atomization Cell for Atomic Fluorescence Spectrometry," *Applied Spectroscopy*, vol. 49, No. 8, 1995.

Li, Gangqiang, Yixiang Duan and Gary M. Hieftje, "Space–Charge Effects and Ion Distribution in Plasma Source Mass Spectrometry," *Journal of Mass Spectrometry*, vol. 30, pp. 841–848, 1995.

Duan, Yixiang, Yimo Li, Xiaodan Tian, Hanqi Zhang and Qinhan Jin, "Analytical Performance of the Microwave Plasma Torch in the Determination of Rare–earth Elements with Optical Emission Spectrometry," *Analytica Chimica Acta*, vol. 295, pp. 315–324, 1994.

Jin, Qinhan, Hanqi Zhang, Ying Wang, Xianglin Yuan and Wenjun Yang, "Study of Analytical Performance of a Low–powered Microwave Plasma Torch in Atomic Emission Spectrometry," *Journal of Analytical Atomic Spectrometry*, vol. 9, pp. 851–855, Aug. 1994.

Duan, Yixiang, "Development and Investigation of Microwave Plasma Techniques in AnalyticalAtomic Spectrometry," Ph.D dissertation, Jilin University, Changchun, P.R. China, Jun., 1994.

"Air Monitor Instantly Detects Beryllium, Other Elements", Los Alamos National Laboratory Daily News Bulletin, Jan. 4, 2000.

\* cited by examiner

MICROWAVE PLASMA MONITORING SYSTEM FOR REAL-TIME ELEMENTAL ANALYSIS

This application claims the benefit of U.S. Provisional Application No. 60/186,428, filed Mar. 2, 2000, and U.S. Provisional Application No. 60/186,458, filed Mar. 2, 2000.

TECHNICAL FIELD

This invention relates to a method and apparatus for elemental analysis. This invention relates more particularly to a method and apparatus with microwave plasma source for monitoring of air and liquid streams for elemental contaminants including transition metals, rare earth elements, actinides, or alkali and alkaline earth elements.

This invention was made with government support under Contract No. W-7405ENG-36 awarded by the U.S. Department of Energy. The government has certain rights in the invention.

BACKGROUND ART

Because of increasing global efforts to protect the environment and increasing concerns for worker safety, there is increasing need for capability for real-time monitoring of air and liquid streams for the presence of transition metals, rare earth elements, actinides, or alkali and alkaline earth elements. There is a continuing and increasing need for sensitive, real-time, portable monitoring devices for detection of the presence of elements in industrial waste streams.

In one particular example, beryllium is extracted from beryl ore and converted to beryllium hydroxide for the production of metal alloys, oxides, ceramics, and pure beryllium for use in various industries and military applications. Because of increased regulatory activity and awareness of health hazards during extraction and production of beryllium and during industrial and commercial use of beryllium products, it is important to be able to accurately evaluate workplace explosures in a timely manner.

Several methods of monitoring air for the presence of beryllium or other trace elements have been developed.

High volumes of air for sampling can be drawn through filters at high flow rates. After ranges of time from minutes to hours, the filters can be taken off location for laboratory analysis.

Inductive plasma spectrometry has been used to analyze elements from a plasma produced by application of an electromagnetic field to a plasma gas; see e.g., U.S. Pat. No. 4,844,612 (Durr and Rozain, Jul. 4, 1989).

Microwave plasmas have been used for trace element monitoring. Microwave plasmas sustained in a portion of an undiluted furnace exhaust flow have been used for continuous emission monitoring for trace metals in furnace exhaust by atomic emission spectroscopy. These waveguide devices are constructed of refractory materials compatible with high-temperature environments and are mountable inside the furnace exhaust ducts. See, e.g., U.S. Pat. No. 5,671,045 (Woskov, et al., Sep. 23, 1997) which is a continuation of U.S. Pat. No. 5,479,254.

Fused quartz fiber optics in close proximity to a plasma flame have been used to transmit UV through visible emissions to three spectrometers for simultaneous monitoring of several metals. This is disclosed in Woskov, P. P., D. Y. Rhee, P. Thomas and D. R. Cohn, "Microwave plasma continuous emissions monitor for trace-metals in furnace exhaust," *Rev. Sci. Instrum.*, 67 (10), Oct. 1996, American Institute of Physics).

Several methods of monitoring liquid streams have been disclosed in the literature. These include introduction of vapors generated from liquids to be sampled into inductively coupled plasma source atomic emission spectrometers for analysis.

However, there is still a need for sensitive, real-time, portable monitoring devices for detection of the presence of elements in ambient air and liquid streams and a need for economical, energy-efficient monitoring devices.

Therefore, it is an object of this invention to provide an apparatus and method for analysis of air or liquid streams for presence of various elements.

It is another object of this invention to provide such an apparatus and method particularly for sensitive, real-time, on-site monitoring of air for the presence of beryllium.

It is a further object of this invention to provide a reliable, low-energy microwave plasma monitoring apparatus and method.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims which are intended to cover all changes and modifications within the spirit and scope thereof.

DISCLOSURE OF INVENTION

To achieve the foregoing and other objects, and in accordance with the purposes of the present invention, as embodied and broadly described herein, there has been invented a process for analyzing ambient air or other gas samples, in a microwave powered plasma torch without use of an additional carrier gas. There has also been invented an apparatus for analyzing ambient air, other gas samples, or nebulized and desolvated liquids wherein a novel arrangement of plasma gas and sample gas conduits is used to enhance dependability of the plasma. This apparatus embodiment of the invention has a concentric arrangement of plasma gas and sample gas conduits so as to provide a sheath of plasma gas both within and on the outside of the flow of sample air into the plasma region.

The multiple conduit apparatus of the invention comprises:
  (a) a sample gas conduit positioned to conduct a flow of a sample gas to a plasma region;
  (b) a first plasma gas conduit coaxially positioned within the sample gas conduit;
  (c) a second plasma gas conduit positioned such that the sample gas conduit is within the second plasma gas conduit;
  (d) a microwave energy source sufficient to generate a plasma in the plasma region;
  (e) a microwave transmitter connecting said microwave energy source to the second plasma gas conduit; and
  (f) analytical instrumentation connected to receive signals from the plasma region.

The microwave plasma torch can either be contained within a sealed housing or can be operated in ambient air at ambient pressures.

The microwave plasma torch of this invention can be operated continuously for real-time analysis of air.

The apparatuses and methods of the present invention can be used wherever there is a need for monitoring air for the presence of minor amounts of elements, particularly transition metals, rare earth elements, actinides, and alkali and alkaline earth elements. The invention apparatus can also be used to monitor for the presence of halogens, sulfur and silicon. The invention apparatuses and methods are more particularly useful for monitoring air for the presence of beryllium.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

BEST MODES FOR CARRYING OUT THE INVENTION

It has been discovered that ambient air can be sampled and analyzed for presence of transition metals, rare earth elements, actinides, or alkali and alkaline earth elements without use of additional sample carrier gases. This can be done using a microwave powered plasma torch with appropriately arranged conduits for the plasma gas and sample gas (generally ambient air) using equipment small enough to be easily portable.

It is understood that the microwave plasma torch can be operated in either an upright position with the plasma region above the gas conduits, in a sideways position with the plasma region laterally positioned with respect to the gas conduits, or in an upside down position with the plasma region below the gas conduits. An upright position is generally presently preferred, and for convenience of description, the invention appratus is shown in the drawings and described as being in the upright position, with differences in equipment or arrangement of elements for other positions described when a different position of the microwave plasma torch would make a difference. The terms "above", "below", "upper", "lower", "at the top" and "at the bottom" will be used with the understanding that an upright position has been selected merely for convenience of description, not as a limitation.

Figure 1:
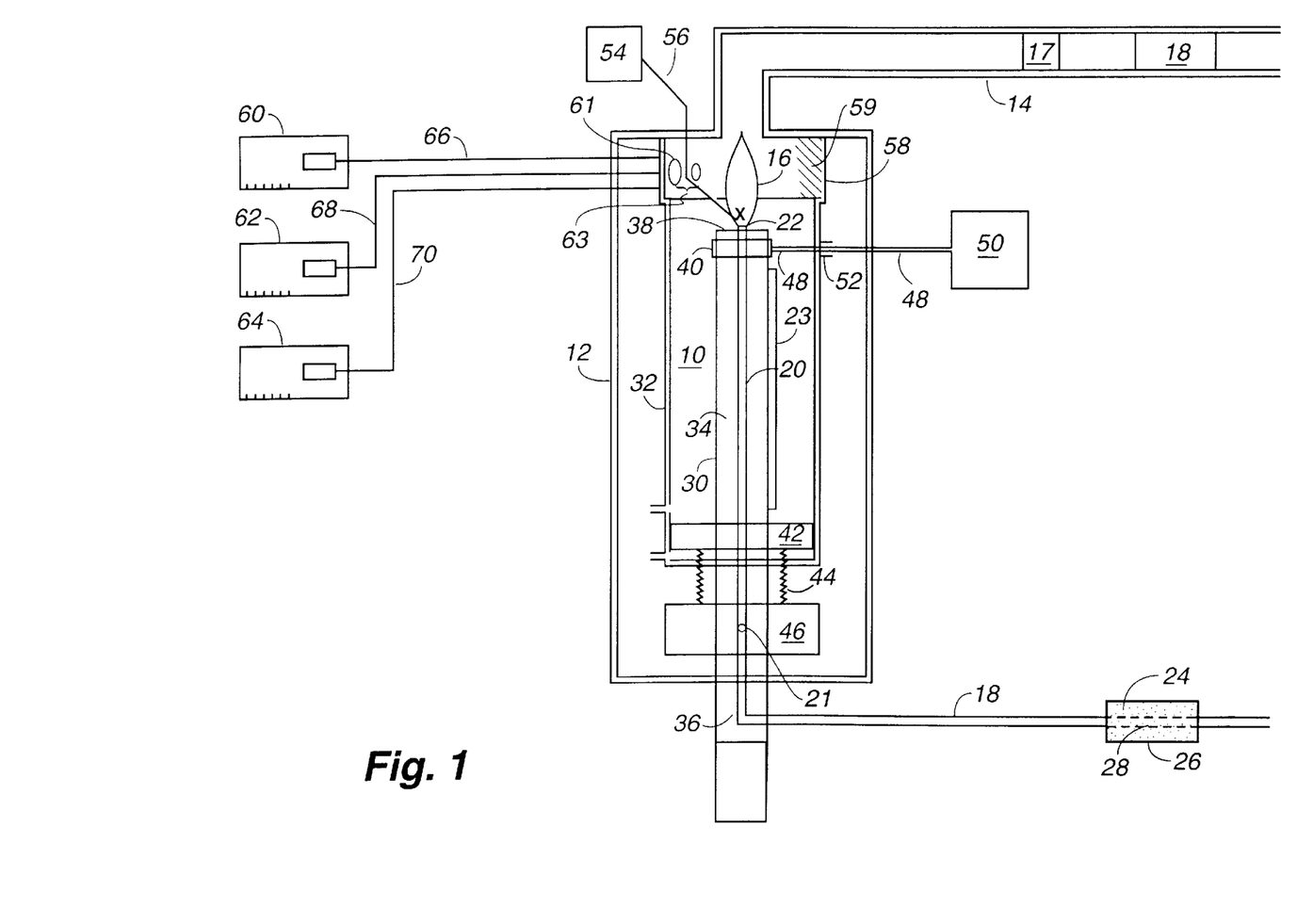
FIG. 1 is a schematic of an example invention device wherein no additional carrier gas is needed for transport of the sample to the plasma region.

FIG. 1 is a schematic drawing of an apparatus which can be used to analyze air for the presence of elemental contaminants in a microwave powered plasma torch without use of additional sample carrier gas. With reference to FIG. 1, a plasma torch 10 is positioned within a sealed housing 12 with a seal housing outlet conduit 14. Use of a sealed housing 12 is useful when the sample gas (the air or other gas containing the analyte to be monitored) is to be sucked or drawn through the microwave plasma torch 10 from the bottom to the top where the plasma region 16 is located. A pump 18 is positioned on a sealed housing outlet conduit 14 so as to provide a negative pressure within the sealed housing 12 sufficient to draw the sample gas or plasma gas or both through the device.

A sealed housing 12 can also be useful if the invention apparatus is to be used in a harsh environment. Generally, when a positive pressure of sample gas and plasma gas is to be pumped through the apparatus from below, a sealed housing is not necessary.

Whether the pump is positioned downstream or upstream of the plasma torch, any pump capable of maintaining the desired flow rates and which does not impede or interfere with transport of the elements or particles contained within the sample gas can be used.

The sample gas to be tested is circulated through the sample gas conduit 20 into the plasma torch 10. The sample gas conduit 20 has an open upper end 22 where, in the embodiment of the invention depicted in FIG. 1, the negative pressure in the sealed housing 12 causes the sample gas to circulate upward into the plasma region 16.

The sample gas conduit 20 does not necessarily have to be made of an electrically conductive material, but it should be relatively inert to the air or other gas to be sampled. Suitable materials include, but are not limited to, copper, brass, aluminum, alumina, stainless steel, silver, gold, and mixtures and alloys thereof, and quartz and ceramic materials.

The flow rate of the sample gas can be controlled by any suitable means such as a flowmeter 17 in the sealed housing outlet conduit 14 or, in the case of a positive pressure of sample gas being introduced at the bottom of the plasma torch, a flowmeter in the conduit 20 through which the sample gas is being transported to the plasma torch 10. A flow rate in the range from greater than 0 to about 10 liters per minute can be used, depending upon the shape of the plasma desired, the kind of plasma gas employed, the size of the conduits, the sensitivity desired, and the particle density in the sample gas. A sample gas flow rate in the range from about 0.05 liter per minute to about 4.0 liters per minute is generally presently preferred. The sample gas and the plasma gas can be introduced simultaneously at different rates according to which flow rate ratios maximize stability of the plasma and provide the amount of sample gas needed for accurate measurement of elements therein.

If desired, the sample gas to be monitored or tested can be pretreated as needed. The example in FIG. 1 depicts a dessicating system which can be incorporated in the sample gas conduit 20 to dry the sample gas before introduction of the sample gas into the plasma region 16. As shown in FIG. 1, a membraneous conduit 24 is put into the sample gas conduit 20 so that the sample gas to be tested is circulated through the membraneous conduit 24. The membraneous conduit 24 is encased in a larger conduit 26 or molecular sieve which is filled with particles of a dessicant 28 such as calcium carbonate, copper sulfate, or any suitable commercially available dessicant such as Dryrite®.

Other methods of drying the sample gas, such as placing two or more commercial dryers in series in the sample gas conduit, can be employed as needed.

If there is a very low concentration of the element to be monitored in the sample gas, then it may be desired to concentrate the sample gas by using impact, electrostatic or ultrasonic concentrators to obtain more accurate detection and measurement of the element in the sample gas.

Any suitable means for delivering the plasma gas into the plasma formation area can be used. Pressurized plasma gas can be released into the plasma gas conduit, or plasma gas can be pumped into the plasma gas conduit.

The flow rate of the plasma gas can be controlled by any suitable means such as a flowmeter in the conduit transporting the plasma gas into the plasma torch. A flow rate in the range from about 0.1 liter per minute to about 10 liters per minute can be used, depending upon the shape of the plasma desired, the kind of plasma gas employed, the size of the conduits, the sensitivity desired, and the analyte density in the sample gas. A plasma gas flow rate in the range from about 0.05 liter per minute to about 4.0 liters per minute is generally presently preferred. The sample gas and the plasma gas can be introduced simultaneously at different rates according to which flow rate adjustments maximize stability of the plasma and provide the amount of sample gas needed for accurate measurement of elements therein.

In the embodiment of the invention shown in FIG. 1, the plasma gas is introduced into a plasma gas conduit 30 which is larger than and coaxially positioned with respect to the portion of the sample gas conduit 20 in the plasma torch 10 so as to provide a plasma gas cavity or anulus 34 between the outer wall of the sample gas conduit 20 and the inner wall of the plasma gas conduit 30. The plasma gas conduit 30 has an inlet end 36 into which the plasma gas is introduced and an open upper outlet end 38 through which the plasma gas exits the plasma gas conduit 30 and enters the plasma region 16.

The sample gas and plasma gas conduits can be any convenient length from only 2 cm long to as much as 200 cm long, depending upon space within which the plasma torch is to be operated and the extent of portability desired. Generally, for operating the plasma torch at ¼ or ¾ wavelength, a length from about 5 cm to about 15 cm is useful.

Alternatively, in another embodiment of the invention, a conduit transporting the plasma gas has a smaller diameter than the sample gas conduit and coaxially positioned with respect to the sample gas conduit so as to form a sample gas cavity in the annulus between the outer wall of the plasma gas conduit and the inner wall of the sample gas conduit.

The outermost conduit (which is the plasma gas conduit 30 in FIG. 1 or the sample gas conduit in the alternative in which the conduit transporting the plasma gas is the one with the smaller diameter) must be made of an electrically conductive material which is compatible with microwave energy transmission. Suitable materials include, but are not limited to, copper, brass, alumina, stainless steel, silver, gold, and mixtures and alloys thereof.

The innermost conduit (the sample gas conduit 20 in FIG. 1 or the plasma gas conduit in the alternative in which the plasma gas conduit is inside the sample gas conduit) can be made of any suitable conducting or nonconducting material, including, but not limited to, copper, brass, aluminum, alumina, stainless steel, silver, gold, and mixtures or alloys thereof, or quartz or ceramic materials. Ceramic materials are useful for withstanding erosion by sample gases.

Any gas which will form a plasma when excited by microwave energy, ignited, then sustained by microwave energy, can be used as the plasma gas. Useful plasma gases include, but are not limited to, argon, helium, nitrogen, or air, depending upon the sensitivity of monitoring needed and upon which analytes are being monitored in the sample gas. Depending upon what kinds of analyzing or monitoring instruments are used, it is desirable to select a plasma gas which will not produce background signals that will make the analyte signals difficult to detect or read. For example, argon is generally most useful when the sample gas is air which is being monitored for trace amounts of beryllium because of the plasma temperatures and helium is generally most useful as a plasma gas when the sample gas is air which is being monitored for trace amounts of silicon because helium provides very high excitation energies.

The plasma gas can be pumped through the plasma gas conduit inlet 36 into the plasma gas anulus 34 with a pump pushing it into or by simply relying upon the negative pressure created in the sealed housing 12 to pull the plasma gas into the plasma region 16. However, generally the plasma gas is introduced into the plasma gas conduit 30 from a pressurized cylinder (not shown) and thus is under positive pressure as it enters the plasma gas conduit 30 through the plasma gas conduit inlet 36.

In an alternative to the embodiment of the invention shown in FIG. 1, at least one hole 21 near the base of the sample gas conduit 20 can be used to allow a portion of the plasma gas from the plasma gas conduit 30 to be admitted to the sample gas conduit 20 so as to mix with the sample gas for transport up the sample gas conduit 20 to the plasma region. The positive pressure of the plasma gas from a pressurized container, if greater than the sample gas pressure, can be used to accomplish intermingling of the plasma gas with the sample gas. Otherwise, pressure of the sample gas flowing upward in the sample gas conduit 20 can pull plasma gas into the sample gas conduit 20 by a Venturi effect.

Proximate to the upper end 22 of the sample gas conduit 20 and the upper end 38 of the plasma gas conduit 30, a collar 40 of electrically conductive material is positioned around the plasma gas conduit 30. One or more refractory spacers are positioned between the collar 40 and plasma gas conduit 30. The collar 40 needs to be close enough to the upper end 22 of the plasma gas conduit 30 to permit effective delivery of microwave energy to the plasma region 16 and to avoid setting up interferences in the microwaves traveling longitudinally in the plasma torch 10.

In the embodiment of the invention shown in FIG. 1, the plasma gas conduit 30 serves as the conductance tube for the microwave energy. A moveable microwave reflector 42 is moveably, or more particularly, slidably, connected to the plasma gas conduit 30, proximate to the lower end of the plasma gas conduit 30 so that the length of the conductance tube between the collar 40 and the microwave reflector 42 can be adjusted to a length equal to an odd number of quarter fractions of the wavelength. For example, the torch can be operated successfully with a conductance tube length equal to one fourth, three fourths, one and a fourth, one and three fourths, . . . of the wavelength of microwave energy being used. It is generally presently preferred to use conductance tube lengths precisely at the selected wave-length increments for better performance.One-quarter wavelength conductance tube lengths are presently preferred for enabling smaller instrument size.

Any suitable device or method can be used to move the microwave reflector 42 along the length of the plasma gas conduit 30; for example, as shown in FIG. 1, a screw 44 mounted on a base 46 can be used.

A microwave transmitter 48 through which microwave energy can be transmitted connects a microwave source 50 to the conductive collar 40. The transmitter passes through an opening 52 in the housing if housing is used.

The microwave transmitter 48 can be either a coaxial cable, waveguide, or other suitable equipment for transmitting the microwaves from the microwave source 50 to the collar 40.

Any suitable microwave source which can provide microwave energy in the appropriate range can be used in the invention apparatuses. Generally useful microwave sources include, but are not limited to, microwave oscillators, magnetrons, or klystron generators. Presently preferred as a microwave source is a magnetron because of the wide range of amounts of power which can be produced.

The invention apparatus can be operated using low levels of microwave energy, depending upon what degree of sensitivity is needed, selected flow rates of plasma and sample gases, choice of plasma gas and kind of analyte being monitored. The energy source can be operated in pulsed or continuous wave mode. Energy levels in the range from about 20 to about 300 Watts can be used. Generally presently preferred are energy levels in the range from about 100 to about 300 Watts when air is being monitored for beryllium and argon is used as the plasma gas. Monitoring of samples from liquid streams which have been nebulized and entrained in carrier gas has been successfully conducted operating the plasma torch in the range from about 50 W to about 200 W. Appropriate adjustment of power to the torch can minimize reflected power, which is typically less than 10 W during operation.

An electrical semiconductor cooling chip or other suitable cooling device 23 can be used to take heat away from the plasma torch, thereby enabling operation at either high or low power levels.

Microwaves in the range from about 1000 MHz to about 10,000 MHz can be used to activate and sustain the plasma. Presently preferred are microwaves in the range from about 2000 MHz to about 3000 MHz, and presently most preferred is a 2450 MHz frequency.

The plasma is initiated by contact of the plasma gas in the plasma region 16 with a sufficient amount of ignition energy to provide a seed electron. The initiation of the plasma can be accomplished by any suitable means such as contacting the plasma gas in the plasma region 16 with energy from a tesla coil, a laser, UV radiation, or an electrical spark.

In FIG. 1, the plasma initiator 54 has connected thereto an initiator energy conductor 56 which extends through the wall of the sealed housing 12 into the plasma region 16. Depending upon the type of plasma initiator used, the initiator energy conductor can be simply an electrically conductive wire, or any other suitable means of getting energy into the plasma region.

The plasma region 16 is generally in a naturally occurring flame shape or toroidal shape situated above the upper aperture of the plasma gas conduit 30 because the microwave energy is highly focused there.

A chimney 58 may be used to shield the plasma region 16 from air currents or outside gas and to contain and stabilize the plasma. The chimney 58 may be made of any material which can withstand the plasma temperature and is transparent to the spectral wavelength of the analytes being monitored. For example, the chimney may be made of quartz, glass or gallium. Alternatively, if desired, a metal screen 59 can be used to shield the plasma.

The light in the plasma region 16 is focused and collected by any suitable system, depending upon the system set up, what type of signal transmitter is used, and what analysis equipment is used. Various combinations and configurations of optical focusing lenses, optical filters, waveguides, and/or optical fibers can be employed. For example, a collimating lens 61 can be used to direct light from a side-on view of the plasma region into an optical fiber. In a presently preferred arrangement, a double lens focusing apparatus 63 is used to enlarge the beam collection angle.

Any of several types of transmitter can be used to transmit signals from the plasma region to the analysis instrument. What is the most suitable transmitting equipment will depend upon the choice of analytical instrumentation and the type, wavelengths and intensity of the signal to be transmitted.

Generally useful for transmitting signals from the plasma region to an atomic emission spectrometer, monochronometer with a photomultiplier detector or other analytical equipment are focusing tens and fiber optic lines. Alternatively, a light pipe can be used for directing light into a spectrometer. Electrically conductive wires connected to electrodes on either side of the plasma region can be used for transmitting a signal from the plasma region to a potentiometer.

A single signal transmitting line is usually sufficient, particularly when sampling for only a single element or when sequential sampling capability is desired. However, in some particular cases, a plurality of transmission lines or other devices for transmission of the signals from the plasma region to the analyzing equipment can be used if needed for a particular monitoring application. For example, atomic and ionic spectral lines have different optimum observation heights and need to be monitored at different positions. Also, elements with significant differences in chemical and physical properties may need to be monitored using different equipment.

The light from the plasma region 16 is analyzed by any suitable means, depending upon the spectral wavelengths of the analytes and the desired speed of analysis. An atomic emission spectrometer with a photomultiplier tube or a charge-coupled detector (CCD) or mass spectrometer can be used. Generally presently preferred when analyzing air for presence of trace amounts of beryllium is an integrated small spectrometer with a CCD detector or a monochronometer with a photomultiplier tube detector. In another generally presently preferred embodiment, when using argon plasma gas to monitor a liquid stream for presence of beryllium, a dual channel spectrometer is used for optical beam dispersal and signal measurement and a linear CCD array detector with 2048 element pixels is used for instantaneous measurements of analyte signals.

When it is already known what the analytes are and it is desired simply to measure concentrations on a production basis, a potentiometer which measures electrical resistance also could be used for signal analysis.

In the example embodiment of the invention shown in FIG. 1, three analytical instruments 60, 62, and 64 receive signals from the plasma region 16 through three fiber optic lines 66, 68, and 70 which each have one end proximate to the quartz glass chimney 58 and are each connected by a distal end to one of the instruments 60, 62, and 64. Or, if no chimney 58 is used, each of the signal transmitting lines are positioned proximate to the plasma region 16.

Any suitable computer control systems can be used for flow meter controls and for processing data from the analytical instruments. Portable computing devices are particularly useful when the invention apparatus is to be used for in-situ sampling or to be transported to multiple sites.

Commercially available software can be used. For example, an OOIBAS 32-bit software package can be used for all data acquisition and control and to provide a realtime interface to the signal processing function. A notebook computer with a 100 kHz sampling frequency DAQ-700 card can be used to show a real time spectrum on its screen and to store data. A CBL-2-NI interface cable can be used to make a connection between the spectrometer and the computer.

The invention device can be operated continuously for as long a period of time as desired with continuous readouts or recording of elements and amounts thereof in the sample gas being circulated through the plasma torch.

It is generally sometimes preferred to not use a carrier gas for the sample to be tested because use of the carrier gas would dilute the concentration of the analytes in the air or other sample gas. However, a carrier gas can be used. This is sometimes done in the embodiment of the invention in which the sample gas is sheathed by a plasma envelope in order to maintain the energy density in the plasma region and to help stabilize the plasma.

Any suitable carrier gas which is stable in monoatomic form and has potential for high energy in a plasma such as argon, helium, neon, xenon and krypton can be used. Also, diatomic nitrogen can also be used as the carrier gas. A mixture of different carrier gases can be used.

Generally it is better to use the same gas used as the plasma gas as a carrier gas because the spectrum is simpler than that obtained with multiple gases.

When a carrier gas is used, it is mixed with the sample gas prior to or during introduction of the sample gas into the sample gas conduit. The ratio of sample gas to carrier gas selected will depend upon the plasma gas used, analyte concentration, and the sensitivity required.

Figure 2:
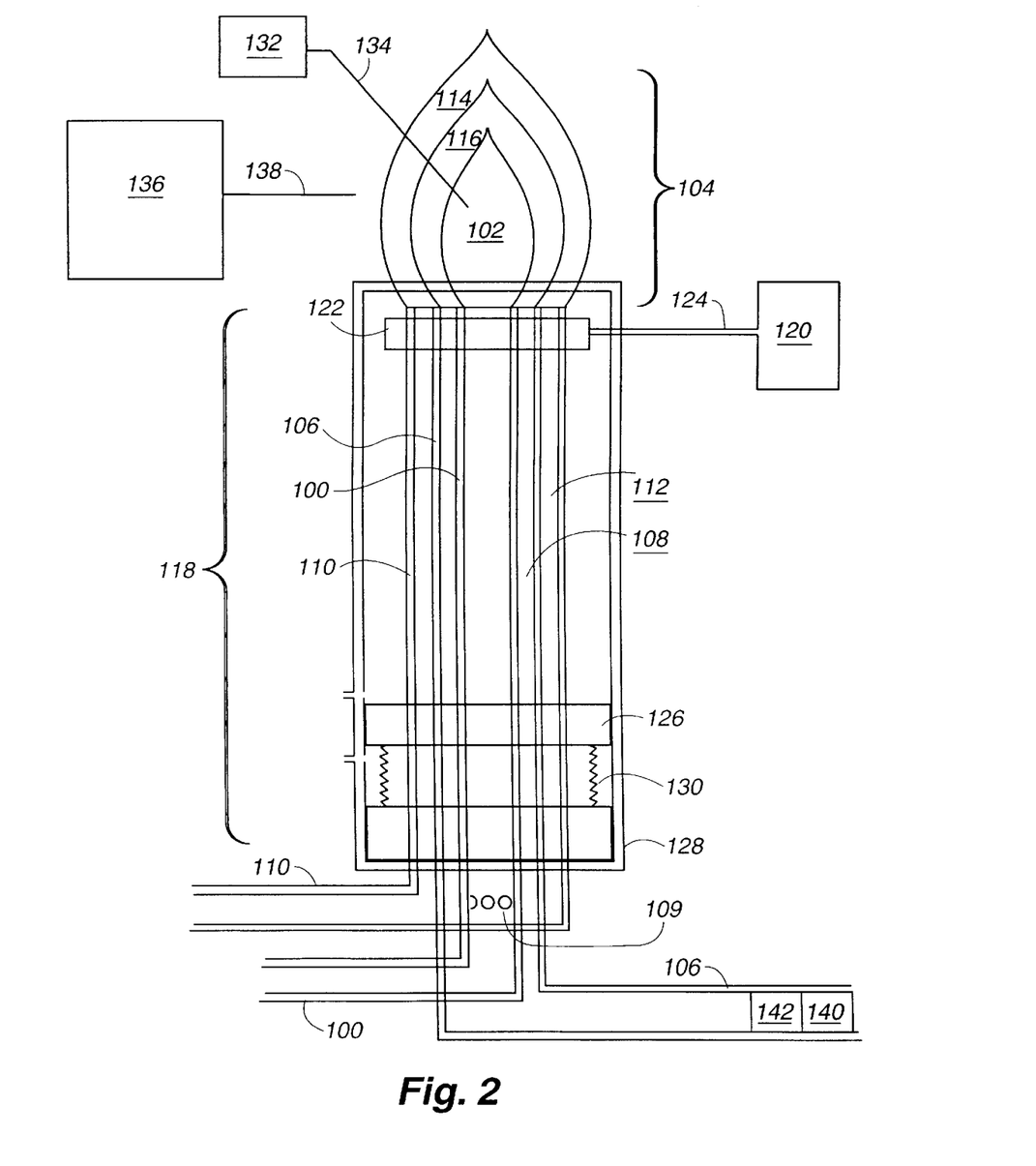
FIG. 2 is a schematic of an example of an invention device having three concentrically arranged conduits to permit the sample gas flow into the plasma region to be sheathed by two plasma gas flows.

In another embodiment of the invention, a flow of the gas (usually air) to be tested or monitored is conducted through the apparatus in such a manner as to be shielded or enveloped by an active plasma on two sides of the sample gas entering the plasma region. This can be done, for example, using three co-axially arranged tubes or conduits as shown in FIG. 2.

A centermost first conduit 100 transports plasma gas to the center 102 of a plasma region 104 where it is in intimate contact with the air or gas to be sampled. The air or other gas to be sampled is transported to the plasma region 104 through a second conduit 106 having a larger diameter than the centermost first conduit 100 and coaxially positioned with respect to the centermost first conduit 100 so as to form an anulus 108 between the first conduit 100 and the second (sample gas) conduit 106. The sample gas conduit 106 is generally longer than the centermost, first conduit 100, with the end of the sample gas conduit 106 extending upward beyond the end of the first conduit 100. When the sample gas conduit 106 longer than the first plasma gas conduit 100, there is some mixing of the plasma gas from the first conduit 100 with the sample gas from the sample gas conduit 106 prior to entry of the plasma gas and sample gas into the plasma region 104.

In an alternative embodiment, if desired, the innermost central conduit 100 carrying plasma gas can have a plurality of openings 109 arranged about the circumference near the lower end of the conduit 100 for the purpose of allowing plasma gas from the conduit 100 to be mixed with the sample gas in the sample gas conduit 106.

The second (sample gas) conduit 106 is in turn surrounded by a third (plasma) conduit 110, which is larger in diameter than the second conduit 106 and coaxially arranged with respect to the second conduit 106 so as to form an anulus 112 between the outer wall of the second conduit 106 and the inner wall of the third conduit 110. The third conduit 110 is generally the same length as the second conduit 106 so that the upper ends of both are at approximately the same level. A second portion of plasma gas is transported through the annulus 112 to the plasma region 104 where it forms an outer sheath 114 about the air or other sample gas flow 116 into the plasma region 104.

The triple-conduit plasma torch 118 of this embodiment of the invention can be otherwise set up and operated in a manner similar to that in which the above-described embodiments are set up and operated. Any suitable conventional microwave power source 120 is connected to a conductive collar 122 using a microwave transmitter 124 or any other suitable connector. The conductive collar 122 is positioned on the outer wall of the outermost third conduit 110 near enough the upper ends of the three conduits to permit excitation of the plasma proximate to the end where the plasma region 104 is to form. There is a refractory spacer between the conductive collar 122 and the outer wall of the third conduit 110. As in the other embodiments of this invention, it is generally advantageous to have the upper ends of the plasma gas conduits 106 and 110 aligned (extending to the same height) with each other. The sample gas conduit 106 is not necessarily aligned with the plasma gas conduits 106 and 110, and is generally somewhat longer than the plasma gas conduits 106 and 110 to allow some mixing of the sample gas and plasma gas. Microwaves from the microwave power source 120 are reflected by a microwave reflector 126 located near the lower end of the three conduits at a distance from the conductive collar 122 equal to an odd number of quarters of the wavelength being used for effective microwave energy resonance. The microwave reflector 126 is mounted upon a base 128, such as, for example, a screw 130, in such a manner as to permit adjustment of the distance between the collar 122 and the microwave reflector 126 by moving the microwave reflector 126 longitudinally on the three conduits.

The plasma is initiated as described for other embodiments of the invention using an initiator energy source 132 and an initiator energy conductor 134 which extends into the plasma region 104.

Instrumentation 136 for analyzing signals from the plasma region 104 is positioned so as to receive signals through, in this particular example, a fiber optic cable 138.

Choices of microwave power and wavelengths, plasma gas, plasma and sample gas flow rates, and analytical instrumentation of the types described for the first embodiments of the invention are used with this multiple-plasma-gas conduit embodiment of the invention.

Figure 3:
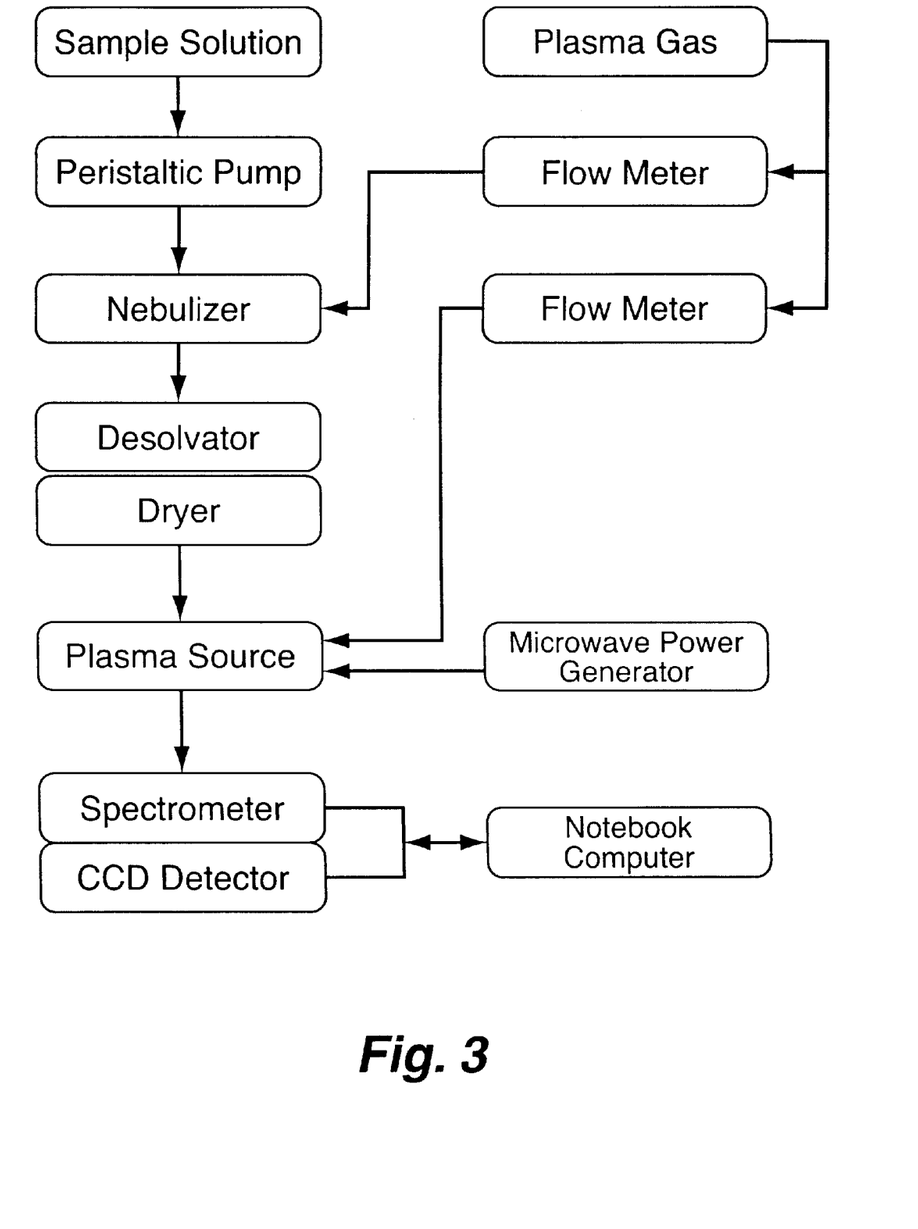
FIG. 3 is a flow chart showing process flow for use of the invention to monitor a liquid stream.

FIG. 3 is a flow chart for one particular example of use of the invention to monitor and analyze a liquid stream. Samplings from standard solutions for calibration or from streams are transported into a nebulizer using a peristaltic or other suitable pump or a flow injection valve. The liquid sample is first nebulized in any convenient nebulizer such as an ultrasonic nebulizer to produce an aerosol. The ultrasonic nebulizer can be cooled using semiconductor chips rather than traditional water chiller methods. Then, in a second subsequent step, the aerosol is desolvated in a two-step desolvation process with a membrane desolvator as a first stage and a sieve sorbent device as the second to further dry the sample. The effectiveness of desolvation steps can be enhanced by pre-heating the aerosal. The sample is then transported to the plasma torch which is configured and operated in accordance with any of the above-described invention embodiments. Alternatively, the nebulized sample can be transported with a carrier gas directly to the plasma torch without further drying.

In the particular example depicted in the flow chart of FIG. 3, a portion of plasma gas is combined with the nebulized sample as a carrier gas prior to further drying of the sample gas. That provides for an intimate mixture of sample gas and plasma gas in the plasma region.

The invention device is portable and can be operated in a continuous operation mode, with a microwave plasma which can be sustained at approximately atmospheric pressure.

Carrier gases, although not necessary for air monitoring, can be used as needed to deliver the samples, which can be air or gas samples, including aerosols, and airborne particulates, through the sample gas conduit into the microwave plasma where they can be analyzed in any of a variety of ways. Low power microwave plasmas can be used.

The invention instrument is less complex than other presently used air monitoring systems, and can be more compact and convenient for on-site, real-time analysis.

While the apparatuses and methods of this invention have been described in detail for the purpose of illustration, the inventive apparatuses and methods are not to be construed as limited thereby. This patent is intended to cover all changes and modifications within the spirit and scope thereof.

INDUSTRIAL APPLICABILITY

The apparatus and method of this invention can be used wherever there is a need for monitoring air for presence of minor amounts of elements, particularly transition metals, rare earth elements, actinides, and alkali and alkaline earth elements.

What is claimed is:

1. An apparatus for elemental analysis comprising:
   (a) a sample gas conduit positioned to conduct a flow of a sample gas to a plasma region;
   (b) a first plasma gas conduit coaxially positioned within said sample gas conduit and wherein said sample gas conduit is longer than said first plasma gas conduit;
   (c) a second plasma gas conduit positioned such that said sample gas conduit is within said second plasma gas conduit;
   (d) a microwave energy source sufficient to generate a plasma in the plasma region;
   (e) a microwave transmitter connecting said microwave energy source to said second plasma gas conduit; and
   (f) analytical instrumentation connected to receive signals from the plasma region.

2. An apparatus for elemental analysis comprising:
   (a) a sample gas conduit positioned to conduct a flow of a sample gas to a-plasma region;
   (b) a first plasma gas conduit coaxially positioned within said sample gas conduit;
   (c) a second plasma gas conduit positioned such that said sample gas conduit is within said second plasma gas conduit and wherein said sample gas conduit is substantially the same length as said second plasma gas conduit;
   (d) a microwave energy source sufficient to generate a plasma in the plasma region;
   (e) a microwave transmitter connecting said microwave energy source to said second plasma gas conduit; and
   (f) analytical instrumentation connected to receive signals from the plasma region.

3. An apparatus for elemental analysis comprising:
   (a) a sample gas conduit positioned to conduct a flow of a sample gas to a plasma region;
   (b) a first plasma gas conduit coaxially positioned within said sample gas conduit;
   (c) a second plasma gas conduit positioned such that said sample gas conduit is within said second plasma gas conduit and wherein said sample gas conduit has at least one hole on its circumference near the base of said sample gas conduit connecting said sample gas conduit with the annulus between said sample gas conduit and said second plasma gas conduit;
   (d) a microwave energy source sufficient to generate a plasma in the plasma region;
   (e) a microwave transmitter connecting said microwave energy source to said second plasma gas conduit; and
   (f) analytical instrumentation connected to receive signals from the plasma region.

4. An apparatus for elemental analysis comprising:
   (a) a sample gas conduit positioned to conduct a flow of a sample gas to a plasma region;
   (b) a first plasma gas conduit coaxially positioned within said sample gas conduit and wherein said first plasma gas conduit has at least one hole on its circumference near the base of said first plasma gas conduit connecting said first plasma gas conduit with the annulus between said first plasma gas conduit and said sample gas conduit;
   (c) a second plasma gas conduit positioned such that said sample gas conduit is within said second plasma gas conduit and;
   (d) a microwave energy source sufficient to generate a plasma in the plasma region;
   (e) a microwave transmitter connecting said microwave energy source to said second plasma gas conduit; and
   (f) analytical instrumentation connected to receive signals from the plasma region.

5. An apparatus for elemental analysis comprising:
   (a) a sample gas conduit positioned to conduct a flow of a sample gas to a plasma region;
   (b) a first plasma gas conduit coaxially positioned within said sample gas conduit;
   (c) a second plasma gas conduit positioned such that said sample gas conduit is within said second plasma gas conduit and;
   (d) a microwave energy source sufficient to generate a plasma in the plasma region;
   (e) a microwave transmitter connecting said microwave energy source to said second plasma gas conduit; and
   (f) analytical instrumentation connected to receive signals from the plasma region;
   (g) said apparatus further comprising an electrically conductive collar surrounding the outer surface of a first end of said second plasma gas conduit, said collar connected to said microwave transmitter so as to direct microwaves longitudinally in said second plasma gas conduit.

6. An apparatus for elemental analysis comprising:
   (a) a sample gas conduit positioned to conduct a flow of a sample gas to a plasma region;
   (b) a first plasma gas conduit coaxially positioned within said sample gas conduit;
   (c) a second plasma gas conduit positioned such that said sample gas conduit is within said second plasma gas conduit;
   (d) a microwave energy source sufficient to generate a plasma in the plasma region;
   (e) a microwave transmitter connecting said microwave energy source to said second plasma gas conduit; and
   (f) analytical instrumentation connected to receive signals from the plasma region;
   (g) said apparatus further comprising a moveable microwave reflector moveably connected to said second plasma gas conduit proximate a second end of said second plasma gas conduit.

7. An apparatus for elemental analysis comprising:

(a) a sample gas conduit positioned to conduct a flow of a sample gas to a plasma region;

(b) a first plasma gas conduit coaxially positioned within said sample gas conduit;

(c) a second plasma gas conduit positioned such that said sample gas conduit is within said second plasma gas conduit;

(d) a microwave energy source sufficient to generate a plasma in the plasma region;

(e) a microwave transmitter connecting said microwave energy source to said second plasma gas conduit; and (f) analytical instrumentation connected to receive signals from the plasma region;

(g) said apparatus further comprising a cooling device positioned and connected so as to take heat away from said apparatus.

8. The apparatus recited in claim 7 wherein said cooling device is an electrical semiconductor cooling chip.

9. An apparatus for elemental analysis comprising:

(a) a sample gas conduit positioned to conduct a flow of a sample gas to a plasma region;

(b) a first plasma gas conduit coaxially positioned within said sample gas conduit;

(c) a second plasma gas conduit positioned such that said sample gas conduit is within said second plasma gas conduit;

(d) a microwave energy source sufficient to generate a plasma in the plasma region;

(e) a microwave transmitter connecting said microwave energy source to said second plasma gas conduit; and (f) analytical instrumentation connected to receive signals from the plasma region;

(g) said apparatus further comprising a chimney positioned to shield said plasma region.

10. An apparatus for elemental analysis comprising:

(a) a sample gas conduit positioned to conduct a flow of a sample gas to a plasma region;

(b) a first plasma gas conduit coaxially positioned within said sample gas conduit;

(c) a second plasma gas conduit positioned such that said sample gas conduit is within said second plasma gas conduit;

(d) a microwave energy source sufficient to generate a plasma in the plasma region;

(e) a microwave transmitter connecting said microwave energy source to said second plasma gas conduit; and (f) analytical instrumentation connected to receive signals from the plasma region;

(g) said apparatus further comprising a metal screen positioned to shield the plasma region.

* * * * *